United States Patent [19]

Ranke et al.

[11] Patent Number: 4,881,960
[45] Date of Patent: Nov. 21, 1989

[54] FRACTIONATION OF A HYDROCARBON MIXTURE

[75] Inventors: Gerhard Ranke, Poecking; Elmar Diehl, Munich, both of Fed. Rep. of Germany

[73] Assignee: Linde Aktiengesellschaft, Wiesbaden, Fed. Rep. of Germany

[21] Appl. No.: 188,129

[22] Filed: Apr. 25, 1988

Related U.S. Application Data

[63] Continuation of Ser. No. 893,517, Aug. 5, 1986, abandoned.

[30] Foreign Application Priority Data

Aug. 5, 1985 [DE] Fed. Rep. of Germany ....... 3528071

[51] Int. Cl.$^4$ ................................................ F25J 3/00
[52] U.S. Cl. .......................................... 62/20; 62/23; 62/27; 62/42
[58] Field of Search ................... 62/20, 23, 24, 27, 28, 62/32, 42

[56] References Cited

U.S. PATENT DOCUMENTS

| | | | |
|---|---|---|---|
| 4,278,457 | 7/1981 | Campbell et al. | 62/24 |
| 4,374,657 | 2/1983 | Schendel et al. | 62/28 X |
| 4,420,317 | 12/1983 | Stewart | 62/20 |
| 4,444,576 | 4/1984 | Ryan et al. | 62/20 |
| 4,599,096 | 7/1986 | Burr | 62/20 X |

Primary Examiner—Ronald C. Capossela
Attorney, Agent, or Firm—Millen, White & Zelano

[57] ABSTRACT

For the fractionation of a hydrocarbon mixture, e.g., natural gas rich in a $C_{2+}$ fraction, the hydrocarbon mixture is partially condensed and the thus-produced gas/liquid mixture is separated in a distillation column to produce a gaseous overhead fraction containing lighter hydrocarbons and a liquid bottoms product containing heavier hydrocarbons. In the upper column section, the gas is scrubbed with a physical scrubbing agent which is preferably a part of the bottoms product. A gaseous stream is withdrawn from the middle of the column to give the $C_{4+}$ bottoms product the proper composition for scrubbing purposes. The scrubbing agent is also subcooled to lower the vapor pressure, preferably by a cooler liquid withdrawn from the column.

30 Claims, 2 Drawing Sheets

FRACTIONATION OF A HYDROCARBON MIXTURE

This application is a continuation of application Ser. No. 893,517 filed Aug. 5, 1986, now abandoned.

BACKGROUND OF THE INVENTION

This invention relates generally to a process for the fractionation of a hydrocarbon mixture, for example, natural gas in a distillation column to produce a gaseous overhead fraction containing lighter hydrocarbons and sour gases, if present, and a liquid bottoms product containing heavier hydrocarbons.

It is conventional, for example, in the fractionation of a methane-containing gaseous mixture rich in $C_{2+}$, to cool the crude gas against fractionation products and external refrigeration so as to condense the hydrocarbons. In this process, depending on temperature and pressure, the light components, such as, for example, $N_2$, $CH_4$, and $C_2H_6$, preferentially remain in the gaseous phase. This gas/liquid mixture is then fractionated in a distillation column, i.e., a demethanizer, into a $C_{2+}$ fraction as the bottoms product and a gaseous $C_1$ fraction as overhead.

In order to improve the yield in $C_2$, it is conventional to introduce at the head of the column a reflux stream obtained by condensation of the overhead product, the latter being comprised primarily of $CH_4$ and $C_2H_6$. However, obtaining this reflux condensate is very costly since very low temperatures are required for condensation.

Two processes, in principle, have been used for the formation of the reflux. According to one process, a partial stream of the overhead product is condensed by means of external refrigeration. This requires, depending on pressure and composition, a methane or $C_2$ refrigeration cycle, optionally coupled with a $C_3$ refrigeration cycle. High initial investment and operating costs are involved in the installation of a separate low temperature refrigeration cycle. Moreover, the internal recycle in the column is considerably increased. The yield of $C_2$ is also impaired unless the $CH_4$ is condensed at the head of the column. However, $CH_4$ condensation is costly from an energy viewpoint especially if $N_2$ is present in the feed gas. For further details, reference is invited to U.S. Pat. No. 4,582,517.

In accordance with the other process, the precooled gas, after separation of condensate, is subjected to engine expansion in an expansion turbine to produce a liquid fraction which is introduced as reflux to the head of the column. This expansion method has the drawback that the gas expanded in the turbine must be recompressed in certain instances before being discharged. In case of gases having a high content of $C_{2+}$ hydrocarbons, such as, for example, gas associated with petroleum formations, the amount of gas remaining after partial condensation is relatively small. Thus, only a minor refrigerating value can be gained therewith by expansion of such small gaseous fractions. For further details of this expansion process, reference is invited to U.S. Pat. No. 4,278,457.

In both processes, very low temperatures of $-50°$ to $-120°$ C. are involved. This, in turn, requires thorough prepurification of the feedstock so as to remove congealable components such as water or $CO_2$. Also, expensive low-temperature resistant materials of construction are required.

SUMMARY OF THE INVENTION

An object of one aspect of this invention is to provide an improved process of the type described above, especially a process wherein an overhead fraction of the requisite purity can be obtained in a single and energy-saving fashion.

Upon further study of the specification and appended claims, further objects and advantages of this invention will become apparent to those skilled in the art.

To attain the above objects, the gas, in the upper part of the column section, is scrubbed with a physical scrubbing agent.

Instead of separating, for example, $C_2H_6$ at the head of the distillation column by rectification, as practiced heretofore, the distillation column is preferably provided with a scrubbing section in the upper part of the distillation column so as to permit scrubbing of the $C_2$ fraction in the gas, thereby substantially reducing the amount of $C_2$ in the gaseous overhead stream.

A well known process for separating a mixture in products is the extractive distillation. The main reason for such a distillation is to bypass an azeotropic point by adding a new component to the feed. For a given separation of a given feed only one or two special solvents can be used.

In the new process the solvent on the top of the column does not change the equilibrium of the components, but acts as a physical solvent to absorb the $C_{2+}$ hydrocarbons. The upper section of the column acts as an absorber, only the lower part is a distillation column.

In a preferred embodiment of the general concept of this invention, at least a portion of the bottoms product is recycled to the scrubbing section as the scrubbing medium. Accordingly, in the fractionation of a gaseous mixture rich in $C_2$, the heavy end, $C_{4+}$ of the $C_{2+}$ product obtained at the bottom of the distillation column is employed as the scrubbing agent. The preferable content of $C_2$ and $C_3$-hydrocarbons in the $C_{4+}$ solvent on top of the column depends mainly on the required recovery rate of $C_2$ and $C_3$. In general it is preferable that the $C_{4+}$ fraction contains less than, especially less than 1 mol % $C_2$ and less than 10%, especially less than 3 mol % $C_3$ hydrocarbon. To accomplish this, a secondary gaseous fraction is withdrawn from about the middle of the column, but below the feed point of the feedstock liquid fraction or gas/liquid mixture. This secondary gaseous fraction, in case of a feedstock rich in $C_{2+}$, is rich in $C_2/C_3$ hydrocarbons and is withdrawn at a point which meets the purity requirements with respect to methane and lighter hydrocarbons, e.g., not more than a total of 5 mol % preferably less than 2 mol %. This $C_2/C_3$ gaseous fraction may be liquefied under pressure for purposes of storage and transportation or may be piped to another facility.

According to another preferred feature of this invention, the scrubbing medium is subcooled to reduce its vapor pressure prior to being fed into the column. This cooling step is preferably performed at least in part against liquid having a lower temperature than the bottoms liquid and withdrawn at a point above the bottom of the distillation column. A savings in reboiler heat is thus made possible due to the simultaneous intermediate cooling of the bottoms product scrubbing medium and heating of the withdrawn liquid.

Advantageously, the scrubbing medium is subcooled to a temperature of between $-30°$ and $+30°$ C., preferably to a temperature of $0°$ C. In most instances, cooling to about 0° C. is adequate for scrubbing of $C_2$. By correlating the composition and temperature of the scrubbing medium employed in the column, the $C_2$ and $C_3$ content in the overhead product can be adjusted, as desired.

Preferably, a pressure of between 10 and 42 bar is employed within the distillation column. The upper limit is fixed by the critical pressure of the hydrocarbon mixtures and of the product. In case of heavy hydrocarbons, the critical pressure is in the range of between 35 and 42 bar. The lower pressure range that can be used in the column ranges between 10 and 20 bar. The lower the pressure, the more satisfactory is the phase separation. However, at the same time, the scrubbing of the $C_2$ fraction at the column head becomes impaired; for this reason a tradeoff is generally accomplished on a case-by-case basis.

It is basically possible, in the context of this invention, using a feedstock rich in $C_{2+}$, to effect rough $C_3/C_4$ fractionation simultaneously, so as to obtain a $C_{4+}$ fraction substantially purified of $C_{3-}$ hydrocarbons while permitting the $C_2/C_3$ fraction to contain $C_{4+}$ hydrocarbons in equilibrium concentrations.

The process of this invention can be applied with special advantage to feed gases rich in $C_{2+}$. In general, the process works better with a gas containing only small amounts of lighter components, e.g. 0–40 mol %, preferably 0–20 mol % of $CH_4$ and inerts. In order to compensate the losses of $C_{4+}$ in the overhead stream, the feed gas may also contain some $C_{4+}$.

The process can also be utilized in general during the processing of gases obtained in the expansion of liquids substantially saturated with gas, for example the expansion of gas-loaded petroleum or condensate, or of loaded scrubbing medium from a physical scrubbing operation employed to obtain $C_{2+}$ from natural gas. Such gases are generally of similar composition as the gases mentioned above.

The process of this invention is also applicable to other systems, for example to the removal or production of $CO_2$ from a natural gas rich in $CO_2$ and also containing $C_2$ and $C_{3+}$ hydrocarbons. A gas rich in $CO_2$ for this application means a gas stream containing more than 40 mol % $CO_2$. A typical gas comes from oil fields, where the oil recovery is increased by $CO_2$ injection. The flash gases recovered during the expansion of the produced oil can contain up to 90% $CO_2$ besides of hydrocarbons.

With such gases, the $CO_2$ is withdrawn as a secondary fraction, and $CH_4$ and $C_2$ hydrocarbons are discharged overhead. The bottom product is partly used as scrubbing agent on top of the column, the rest is drawn off as $C_{3+}$ product.

The process of this invention is likewise suitable for obtaining $C_{3+}$ hydrocarbons; in this case, $CH_4$ and $C_2H_6$ are discharged overhead. The $C_{3+}$ product is partly withdrawn in a gaseous phase as a secondary fraction, the heavy end of the feed gas is branched off from the bottom product, the rest is used as scrubbing agent.

This invention is moreover applicable to the recovery of heavy hydrocarbons from refinery waste gases containing mainly $H_2$, $CH_4$, $C_2$ and $C_{3+}$ hydrocarbons.

BRIEF DESCRIPTION OF THE DRAWINGS

The FIG. 1 is a schematic drawing of a preferred embodiment of the invention.

DETAILED DESCRIPTION OF THE DRAWING

Figure 1:
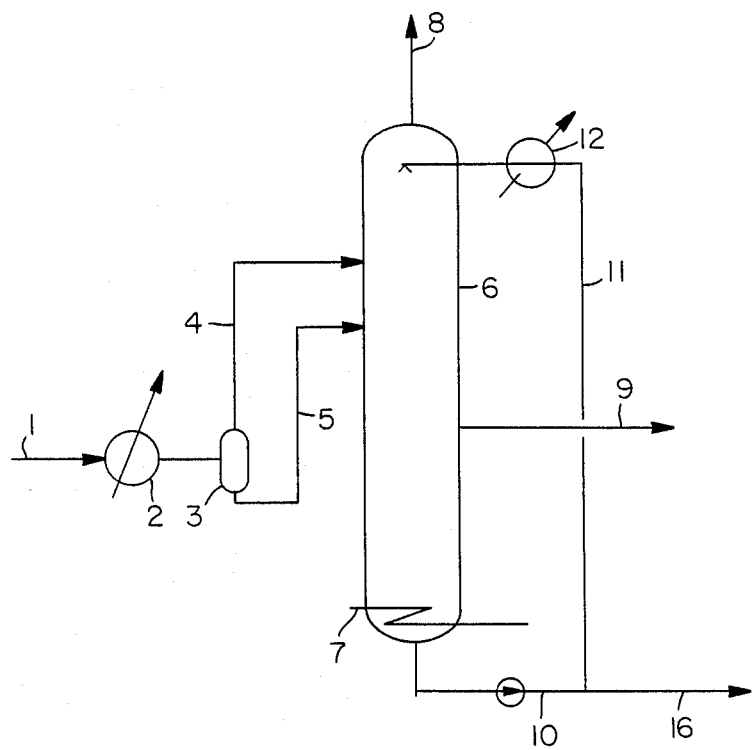

A feedstock rich in $C_{2+}$ is used having the following composition:

| | |
|---|---|
| $N_2 + CH_4$ | 18.08 mol % |
| $C_2H_6$ | 35.83 mol % |
| $C_3H_8$ | 25.78 mol % |
| $C_{4+}$ | 20.31 mol % |
| Total amount | 1000 mol/h |
| Pressure | 28.4 bar |
| Temperature | 30° C. |

This feedstock is conducted via a conduit 1 into a partial condenser cooled by external refrigeration. The partially condensed fluid is passed to a phase separator 3 to form a gaseous phase 4 and a liquid phase 5 which are introduced into a distillation column 6 at points corresponding to their respective compositions and temperatures at the 20 theoretical plate 20 and theoretical plate 17 of this distillation column containing a total of 25 theoretical plates, counting from the bottom.

The distillation column 6 is also equipped with a reboiler 7 which provides the requisite vapor to produce an overhead $C_1$-rich fraction in conduit 8, having the following composition:

| | |
|---|---|
| $C_{1-}$ | 92.0 mol % |
| $C_2$ | 4.8 mol % |
| $C_3$ | 0.3 mol % |
| $C_{4+}$ | 2.9 mol % |
| Total Gas flow | 187 mol/h |
| Pressure | 26.5 bar |
| Temperature | 14° C. |

From the middle of the column, the theoretical plate 12, a $C_{2+}$ product obtained as a secondary fraction via conduit 9, has the following composition:

| | |
|---|---|
| $C_{1-}$ | 1 mol % |
| $C_2$ | 43.0 mol % |
| $C_3$ | 31.7 mol % |
| $C_{4+}$ | 24.3 mol % |
| Total flow | 813 mol/h |
| Pressure | 26.5 bar |
| Temperature | 92° C. |

A $C_{4+}$ fraction withdrawn from the bottom of the column by way of conduit 10 has the following composition:

| | |
|---|---|
| $C_1$ | — mol % |
| $C_2$ | 0.01 mol % |
| $C_3$ | 0.87 mol % |
| $C_{4+}$ | 99.12 mol % |
| Total flow | 800 mol/h |
| Pressure | 26.6 bar |
| Temperature | 196° C. |

About 100% of the $C_{4+}$ fraction is branched off via conduit 11 and, after being cooled in a cooler 12 against external refrigeration to about +5° C., is introduced to the distillation column in the upper section as a scrubbing medium for scrubbing out $C_{2+}$ hydrocarbons. The remaining $C_{4+}$ fraction is discharged in conduit 16 as the product.

Figure 2:
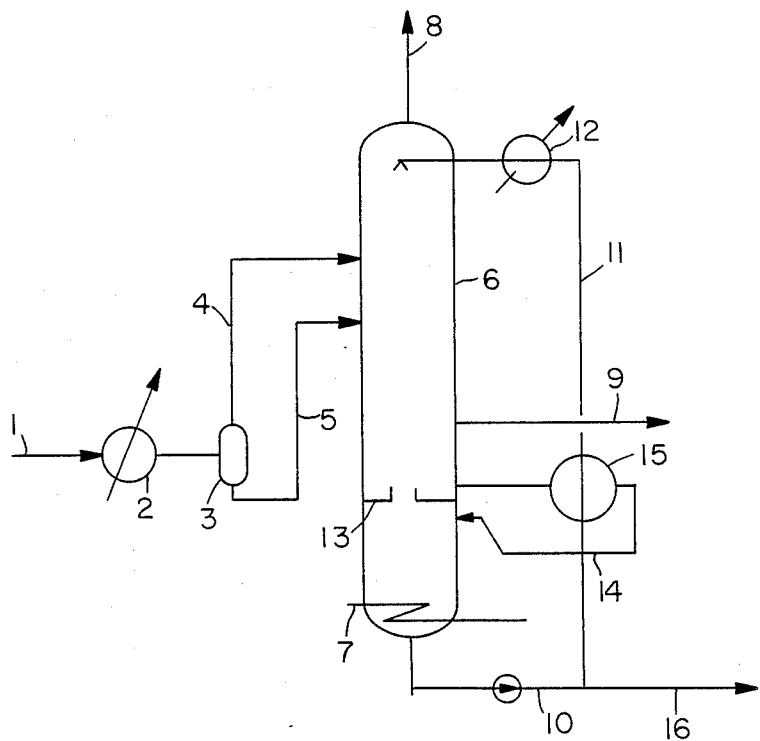
FIG. 2 is a schematic of a modified version of the embodiment of FIG. 1.

In accordance with another preferred feature of this invention illustrated in FIG. 2, a chimney tray 13, e.g., a plate without liquid downcomers, is illustrated in dashed lines in the lower section of the distillation column at the theoretical plate. Liquid is withdrawn above this chimney tray, via a conduit 14 likewise shown in dashed lines, and after being heated against scrubbing medium being cooled in a heat exchanger 15, can be reintroduced into the column below the chimney plate. Accordingly, this cooling stage provides intermediate cooling of the scrubbing medium and lessens the heating load on the reboiler heater 7.

The internal workings of the column consist normally of valve plates or bubble plates, but also packings are possible. The layout of the plates depends on gas and liquid loading.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the fractionation of a gas comprising a mixture of hydrocarbons and inerts in a distillation column having at least one feed point to produce a gaseous overhead fraction containing lighter hydrocarbons and a bottoms product fraction containing heavier hydrocarbons, the improvement comprising the step of passing a physical scrubbing agent into an upper section of the column to scrub out from said gaseous overhead fraction containing lighter hydrocarbons, a heavier hydrocarbon fraction thereof which would otherwise be withdrawn from the column in said gaseous overhead fraction, thereby producing a gaseous overhead fraction containing a lower concentration of heavier hydrocarbons than would be the case without said scrubbing step, and wherein said scrubbing agent introduced into said upper column section contains at least a portion of said heavy hydrocarbon bottoms fraction.

2. A process according to claim 1, wherein said scrubbing agent consists essentially of said heavy hydrocarbon bottoms fraction.

3. A process according to claim 2, wherein said gas comprising a mixture of hydrocarbons, prior to entering the distillation column, is cooled to form liquid and gaseous phases and both of said phases are fed to the distillation column.

4. A process according to claim 3, further comprising withdrawing a secondary gaseous fraction from the middle of the column, but below the lowermost feed point.

5. A process according to claim 4, further comprising subcooling the scrubbing agent prior to passing same into the column.

6. A process according to claim 3, further comprising subcooling the scrubbing agent prior to passing same into the column.

7. A process according to claim 3, wherein said scrubbing medium is cooled to a temperature of between $-30°$ and $+30°$ C.

8. A process according to claim 7, wherein the distillation column is operated at a pressure of between 10 and 42 bar.

9. A process according to claim 2, further comprising withdrawing a secondary gaseous fraction from the middle of the column, but below the lowermost feed point.

10. A process according to claim 9, further comprising liquefying the secondary gaseous fraction under pressure.

11. A process according to claim 9, further comprising subcooling the scrubbing agent prior to passing same into the column.

12. A process according to claim 9, further comprising withdrawing liquid from the distillation column at a point where the liquid is cooler than the bottoms liquid and cooling said scrubbing agent in indirect heat exchange relationship with said withdrawn liquid.

13. A process according to claim 9, wherein said gas comprising a mixture of hydrocarbons is rich in $C_2 +$ hydrocarbons, the $C_2$ and $C_3$ content of the physical scrubbing agent is less than 5 mol % and less than 10 mol %, respectively, and said secondary gaseous fraction is rich in $C_2$ and $C_3$ hydrocarbons having a content of methane and lighter hydrocarbons of not more than 5 mol %.

14. A process according to claim 2, further comprising subcooling the scrubbing agent prior to passing same into the column.

15. A process according to claim 2, further comprising withdrawing liquid from the distillation column at a point where the liquid is cooler than the bottoms liquid and cooling said scrubbing agent in indirect heat exchange relationship with said withdrawn liquid.

16. A process according to claim 1, wherein said gas comprising a mixture of hydrocarbons, prior to entering the distillation column, is cooled to form liquid and gaseous phases and both of said phases are fed to the distillation column.

17. A process according to claim 16, wherein said liquid and gaseous phases are fed separately to the distillation column.

18. A process according to claim 1, further comprising withdrawing a secondary gaseous fraction from the middle of the column, but below the lowermost feed point.

19. A process according to claim 18, further comprising subcooling the scrubbing agent prior to passing same into the column.

20. A process according to claim 18, wherein said overhead gaseous fraction comprises $CH_4$ and $C_2H_6$ and said second gaseous fraction comprises $C_{3+}$ product.

21. A process according to claim 18, wherein said gas comprising a mixture of hydrocarbons further comprises $CO_2$, said gaseous overhead fraction comprises $CH_4$ and $C_2$ hydrocarbons, and said second gaseous fraction comprises $CO_2$.

22. A process according to claim 21, wherein said gas comprises a mixture of hydrocarbons containing more than 40 mol % $CO_2$.

23. A process according to claim 1, further comprising subcooling the scrubbing agent prior to passing same into the column.

24. A process according to claim 23, further comprising withdrawing liquid from the distillation column at a point where the liquid is cooler than the bottoms liquid and cooling said scrubbing agent in indirect heat exchange relationship with said withdrawn liquid.

25. A process according to claim 23, wherein the hydrocarbon fraction to be scrubbed out is a $C_2$ hydrocarbon fraction and the scrubbing agent is sub-cooled to a temperature of about $0°$ C.

26. A process according to claim 1, further comprising subcooling the scrubbing agent prior to passing same into the column.

27. A process according to claim 1, wherein said gas comprises a mixture of hydrocarbons containing 0–40 mol % $CH_4$ and inerts.

28. A process according to claim 1, wherein said gas comprises a mixture of hydrocarbons containing 0–20 mol % $CH_4$ and inerts.

29. A process according to claim 1, wherein said scrubbing agent has a composition different than the hydrocarbon fraction which is scrubbed out of the gas mixture.

30. A process for the fractionation of a gas comprising a mixture of hydrocarbons and inerts in a distillation column having at least one feed point to produce a gaseous overhead fraction containing lighter hydrocarbons and a bottoms product fraction containing heavier hydrocarbons, the improvement comprising passing a physical scrubbing agent into an upper section of the column to scrub out a hydrocarbon fraction which would otherwise be withdrawn from the column in the gaseous overhead fraction and cooling said physical scrubbing agent prior to its delivery to the upper section of the column, said physical scrubbing agent being cooled by indirect heat exchange with a liquid withdrawn from the distillation column at a point where the liquid is cooler than the bottoms liquid.

* * * * *